United States Patent [19]
Jorgenson et al.

[11] Patent Number: 5,359,681
[45] Date of Patent: Oct. 25, 1994

[54] FIBER OPTIC SENSOR AND METHODS AND APPARATUS RELATING THERETO

[75] Inventors: Ralph C. Jorgenson, Mercer Island; Sinclair S. Yee, Seattle, both of Wash.

[73] Assignee: University of Washington, Seattle, Wash.

[21] Appl. No.: 3,224

[22] Filed: Jan. 11, 1993

[51] Int. Cl.$^5$ .................... G02B 6/02; G01J 3/42; H01J 5/16
[52] U.S. Cl. ........................ 385/12; 385/31; 385/39; 385/123; 385/126; 385/127; 385/128; 356/320; 250/227.11; 250/227.14
[58] Field of Search ............ 385/1, 2, 11, 12, 14, 385/31, 38, 39, 47, 48, 123, 126, 127, 128; 356/300, 317, 318, 319, 320, 345, 351; 250/227.11, 227.14, 227.17, 227.19

[56] References Cited

U.S. PATENT DOCUMENTS

| | | | |
|---|---|---|---|
| 4,844,613 | 7/1989 | Batchelder et al. | 356/345 X |
| 4,877,747 | 10/1989 | Stewart | 436/525 |
| 4,929,049 | 5/1990 | Le Goullon et al. | 385/12 X |
| 5,026,139 | 6/1991 | Klainer et al. | 385/12 X |
| 5,047,213 | 9/1991 | Finlan et al. | 422/82.11 |
| 5,067,788 | 11/1991 | Jannson et al. | 385/2 |
| 5,109,442 | 4/1992 | Klainer et al. | 385/12 |
| 5,151,956 | 9/1992 | Bloemer | 385/11 |
| 5,173,747 | 12/1992 | Boiarski et al. | 356/345 X |
| 5,253,037 | 10/1993 | Klainer et al. | 385/12 X |
| 5,268,972 | 12/1993 | Tabacco et al. | 385/123 X |

FOREIGN PATENT DOCUMENTS

| | | | |
|---|---|---|---|
| 326291 | 8/1989 | European Pat. Off. | 385/12 X |
| WO88/06726 | 9/1988 | PCT Int'l Appl. | 385/12 X |

OTHER PUBLICATIONS

Garcés, I. et al., "Four-Layer Chemical Fibre Optic Plasmon-Based Sensor," *Sensors and Actuators.* B7:771–774, 1992. Month of Publication is unavail., requirment is waived.

Cullen, D. C. et al., "A Direct Surface Plasmon–Polariton Immunosensor: Preliminary Investigation of the Non-Specific Adsorption of Serum Components to the Sensor Interface," *Sensors and Actuators.* B1:576–579, 1990. Month of Publication is unavail; requriement is waived.

Culshaw, Brian, "Fibre Optic Sensors and Systems at the University of Strathclyde," *Fiber Optic and Laser Sensors VII.* 1169:2–9, 1989. Month of Publication is unavail; requirement is waived.

Clarricoats, P. J. B. et al. (eds.), *Electronics Letters,* Black Bear Press Limited, Cambridge, England, 1988, vol. 24, pp. 1468–1470. Month of Publication is unavail requirement is waived.

(List continued on next page.)

*Primary Examiner*—Brian Healy
*Attorney, Agent, or Firm*—Seed and Berry

[57] ABSTRACT

There is disclosed fiber optic sensor which detects a sample in contact with the sensor by surface plasmon resonance (SPR) measurements, as well as methods and apparatus relating thereto. The fiber optic SPR sensor of this invention employs a limited range of incident angles and uses incident light having multiple wavelengths. In preferred embodiments, both an in-line transmission-based fiber optic SPR sensor and a terminated reflection-based fiber optic SPR sensor are disclosed. The fiber optic SPR sensor includes a surface plasmon supporting metal layer in contact with an exposed portion of the optical fiber core, and may optionally contain one or more additional layers deposited on the surface plasmon supporting metal layer. In further embodiments, methods are disclosed for detecting a sample by contacting the sample with the fiber optic SPR sensor of this invention, as well as sensing apparatus which contain the fiber optic SPR sensor in combination with a source of electromagnetic radiation of multiple wavelengths and a detection device.

14 Claims, 12 Drawing Sheets

OTHER PUBLICATIONS

Matsubara, Koji, et al., "Optical Chemical Sensor Based on Surface Plasmon Measurement," *Applied Optics.* 27:1160–1163, 1988.

Jorgenson, "Surface Plasmon Resonance as an Optical Probe of the Metal/Dielectric Interface", M.S. Thesis, University of Washington, 1991. Month of Publication is unavail; requirment waived.

Lambeck, "Inegrated opto-chemical sensors", *Sensors and Actuators* B8:103–116, 1992. Month of Publication is unavail; requirement is waived.

Lambeck, "Chemo-optical micro-sensing systems", *SPIE* 1511:100–113, 1991. month of Publications is unavail; requriement is waived.

Villuendas et al., "Optical Fibre Device for Chemical Sensing Based on Surface Plasmon Excitation", *Sensors and Actuators* A21–A23:1142–1145, 1990. Month of Publication is unavail requirement is waived.

Tarassenko et al., "Review of Optical Sensors for Biomedical Applications," Colloquium on Electrochemical Sensors for Biomedical Application, Apr. 1986.

Kang and Dessy, "Slab Waveguides in Chemistry," *Critical Reviews in Analytical Chemistry* 21(6):377–388, 1990. Month of Publication is unavail requirement is waived.

FIBER OPTIC SENSOR AND METHODS AND APPARATUS RELATING THERETO

TECHNICAL FIELD

The present invention is generally directed to a optical fiber sensor and, more specifically, to a optical fiber sensor which utilizes surface plasmon resonance to detect a sample, to a sensing apparatus which employs the optical fiber sensor, and to methods of detecting a sample using the same.

BACKGROUND OF THE INVENTION

Surface plasmon waves are electromagnetic waves which may exist at the boundary between a metal and a dielectric (hereinafter referred to as the "sample"). Such waves can be exited by light which has its electric field polarized parallel to the incident plane (i.e., transverse magnetic (TM) polarized). When the parallel component of the propagation constant of the incident light equals the real part of the surface plasmon wave propagation constant, the incident light resonantly excites the surface plasmon waves, and a fraction of the incident light energy is transferred or dispersed to surface plasmon resonance (SPR). This dispersion of energy depends on both the dielectric constant of the metal and that of the sample in contact with the metal. By monitoring the resonance wavevector of the metal/sample interface, the dielectric constant of the sample (gas or solution) may be obtained. Alternatively, if the sample is contaminated by a chemical species, dielectric constant measurements may provide the concentration of the chemical species in the sample.

Traditionally, SPR has been measured using the Kretschmann configuration Kretschmann and Raether, *Z. Naturforsch. Teil A* 23:2135–2136, 1968). In this configuration, a thin layer of highly reflective metal (such as gold or silver) is deposited on the base of a prism. The metal surface is then contacted with the sample, and the SPR reflection spectra of the sample is measured by coupling TM polarized, monochromatic light into the prism and measuring the reflected light intensity as a function of the angle of incidence. The angle of minimum reflective intensity is the resonance angle at which maximum coupling occurs between the incident light and the surface plasmon waves. This angle, as well as the half-width of the resonance spectrum and the intensity at the angle of minimum reflective intensity, may be used to characterize or sense the sample which is in contact with the metal surface (Fontana et al., *Applied Optics* 27:3334–3339, 1988).

Optical sensing systems have now been constructed based on the Kretschmann configuration described above. Such systems utilize the sensitivity of SPR to changes in the refractive indices of both bulk and thin film samples, as well as to changes in the thickness of thin films. These systems, in conjunction with appropriate chemical sensing layers, have led to the development of a variety of SPR-based chemical sensors, including immunoassay sensors (e.g., Liedberg et al., *Sensors and Actuators* 4:299–304, 1983; Daniels et al., *Sensors and Actuators* 15:11–17, 1988; Jorgenson et al., *IEEE/Engineering Medicine and Biology Society. Proceedings* 12:440–442, 1990), gas sensors (e.g., Liedberg et al., *suprs*; Gent et al., *Applied Optics* 29:2843–2849, 1990), and liquid sensors (e.g., Matsubaru et al., *Applied Optics* 27:1160–1163, 1988).

While the Kretschmann configuration for SPR-based chemical sensors offers significant sensitivity, their relatively large size has severely restricted their application. For example, these bulk optic sensing systems are limited by their use of a coupling prism causing such systems to be relatively large, expensive, and inapplicable for remote sensing applications. Moreover, such sensors generally require a monochromatic light source, are expensive to manufacture due to configuration constraints (such as the presence of a prism), and require that the incident light sweep over a broad range of incidence angles.

Accordingly, there is a need in the art for an improved SPR sensor, as well as for apparatus and methods relating thereto. Specifically, there is the need for an SPR sensor which readily permits remote sensing, is inexpensive, and is free from the limiting constraints now present with existing SPR-based chemical sensors.

SUMMARY OF THE INVENTION

It is an object of the present invention to provide a optical fiber sensor which utilizes SPR to detect a sample in contact with the sensor. It is a further object to provide a sensor which utilizes an optical fiber as the sensor itself, and avoids the use of a coupling prism. An additional object is to provide a fiber optic SPR sensor which utilizes incident light having multiple wavelengths as the excitation energy. Yet a further object is to provide methods and apparatus for detecting a sample using the fiber optic SPR sensor of this invention. The present invention fulfills these objectives, and provides further related advantages.

In one embodiment of this invention, a fiber optic SPR sensing apparatus is disclosed. The apparatus contains a fiber optic SPR sensor in combination with a source of electromagnetic radiation of multiple wavelengths and a detection device. The fiber optic SPR sensor is an optical fiber having a core waveguide and a cladding or cladding/buffer layer surrounding the core waveguide, and wherein the optical fiber has a first end and a second end and at least one sensing area located between the first end and the second end or located at the second end of the optical fiber. The sensing area of the optical fiber is defined by an SPR supporting metal layer which is contact with at least a portion of an exposed surface of the optical fiber core waveguide which is free from the surrounding cladding or cladding/buffer layer. The output from the electromagnetic radiation source is applied to the first end of the optical fiber core waveguide such that the radiation propagates from the first end towards the second end by total internal reflections (TIR), and exits the optical fiber at either the first end or the second end. A detection device monitors the radiation exiting an end of the optical fiber.

In a preferred embodiment, the fiber optic SPR sensor is an in-line transmission-based optical fiber sensor. Such a sensor contains an optical fiber having a core waveguide and a cladding or cladding/buffer layer surrounding the core waveguide, and having an input end and an output end. The sensor has a sensing area located between the input end and output end defined by an SPR supporting metal layer in contact with at least a portion of the optical fiber core waveguide free from the surrounding cladding or cladding/buffer layer. A source of electromagnetic radiation of multiple wavelengths is applied to the input end of the optical fiber core waveguide such that the radiation propagates from the input end towards the output end by TIR. A detection device then monitors the radiation exiting the output end of the optical fiber waveguide.

In a further preferred embodiment, the sensing apparatus of the present includes a terminated reflection-based fiber optic SPR sensor. This sensor contains an optical fiber having a core waveguide and a cladding or cladding/buffer layer surrounding the core waveguide, and having an input/output end and a terminal reflection end. The terminal reflection end is defined by an end face of the core waveguide in contact with a mirrored layer. The sensing area of the sensor is located between the input/output end and terminal reflection end, and is defined by an SPR supporting metal layer in contact with at least a portion of the optical fiber core waveguide free from the surrounding cladding or cladding/buffer layer. A source of electromagnetic radiation of multiple wavelengths is applied to the input/output end of the optical fiber waveguide, and the radiation propagates from the input/output end towards the terminal reflection end by total internal reflections, internally reflects off the mirrored layer in contact with the end face of the core waveguide, and propagates back down the optical fiber waveguide by total internal reflections towards the input/output end. A detection device monitors the radiation exiting the input/output end of the optical fiber waveguide.

In another embodiment of this invention, a method for detecting a sample is disclosed. In this method, a sample was contacted with a fiber optic SPR sensor of the present invention. A source of electromagnetic radiation of multiple wavelengths is applied to one end of the fiber optic SPR sensor and the radiation exiting the sensor is detected.

In yet a further embodiment, the present invention discloses a fiber optic SPR sensor. The sensor has an optical fiber core waveguide and a cladding or cladding/buffer layer surrounding the core waveguide. A sensing area is located between a first and second end of the optical fiber and is defined by an SPR supporting metal layer in contact with at least a portion of the surface of the optical fiber core waveguide free from the surrounding cladding or cladding/buffer layer. In preferred embodiments, the fiber optic SPR sensor is an in-line transmission-based fiber optic SPR sensor or a terminated reflection-based fiber optic SPR sensor.

These and other aspects of this invention will become evident upon reference to the following detailed description and attached drawings.

DETAILED DESCRIPTION OF THE INVENTION

This invention is directed to a optical fiber sensor which detects a sample in contact with the sensor by surface plasmon resonance (SPR) measurements. The present invention is also directed to methods and apparatus relating to the use of the fiber optic SPR sensor to detect a sample. In preferred embodiments, the fiber optic SPR sensor of this invention includes an in-line transmission-based sensor and a terminated reflection-based sensor. The fiber optic SPR sensor of this invention advantageously eliminates the traditional bulk optic prism in favor of an optical fiber design which permits remote sensing and multiplexing between multiple fiber optic SPR sensors.

Figure 1A:
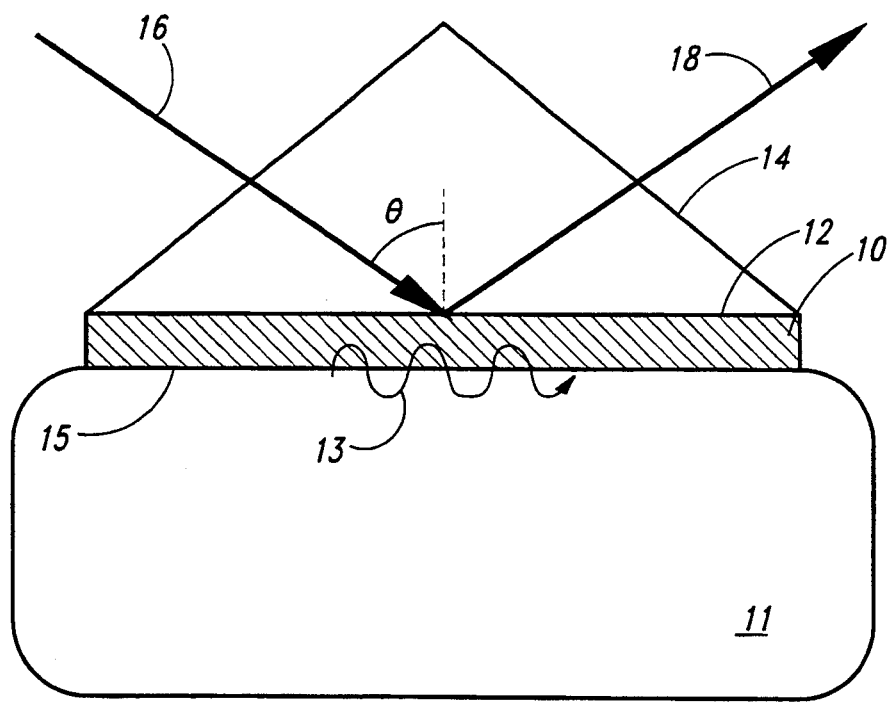
FIG. 1(a) represents the prior art Kretschmann configuration for a bulk optic SPR-based chemical sensor.
Figure 1B:
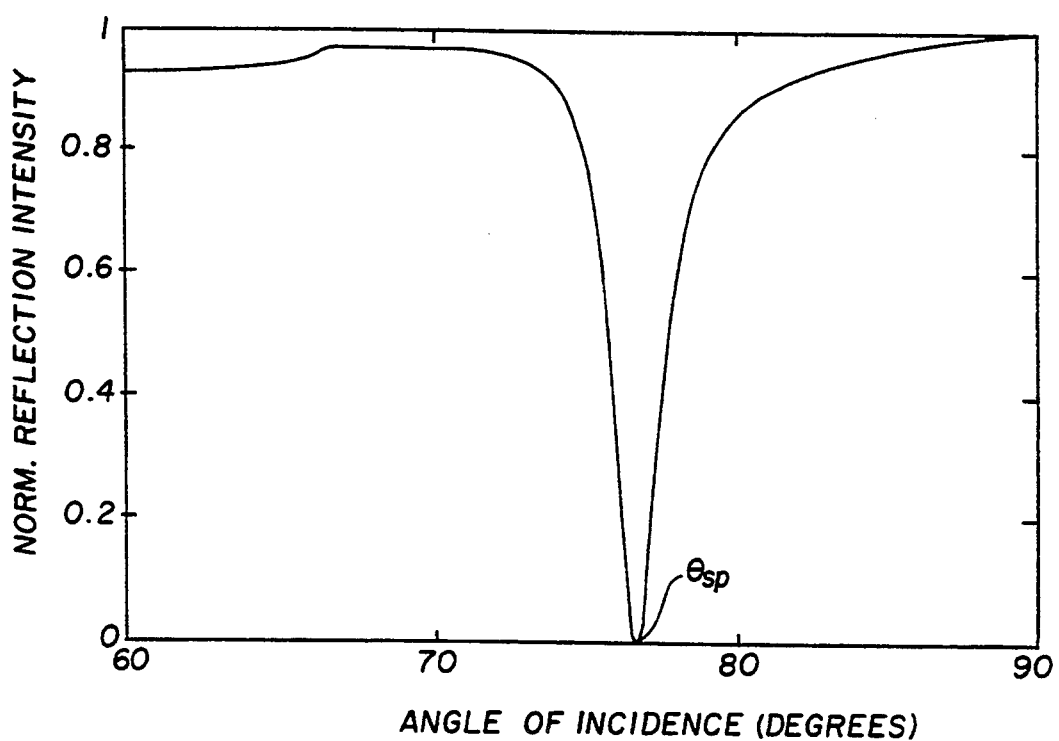
FIG. 1(b) illustrates an SPR reflection spectra obtained from the prior art sensor of FIG. 1(a) for a bulk dielectric of water, a wavelength of 620 nm, a 550 Angstrom-thick silver film, and a fused silica prism.

As mentioned above, prior art SPR-based chemical sensors are generally based on the Kretschmann configuration (see, Kretschmann and Raether, Z. Naturforsch. Teil A 23:2135–2136, 1968). Such a prior art SPR-based chemical sensor is illustrated in FIG. 1(a). Specifically, a highly reflective metal layer (10), such as gold or silver, is deposited on base (12) of prism (14). TM polarized, monochromatic incident light (16) is directed into the prism and reflects off the prism base/metal layer interface. The intensity of reflected light (18) is measured by a detection device (not shown). A sample (11) is brought in contact with exposed surface (15) of metal layer (10), and the monochromatic incident light is directed into the prism at angle $\theta$ with respect to the normal of the metal layer/sample interface. At appropriate angles of incidence, the monochromatic incident light excites surface plasmon waves (13). The SPR reflection spectra obtained from the prior art SPR-based chemical sensor of FIG. 1(a) is represented in FIG. 1(b) by a two-dimensional plot of reflected light intensity versus the angle of incidence. The angle of minimum reflective intensity is the surface plasmon resonance angle ($\theta_{sp}$) at which maximum coupling of energy occurs between the incident light and the surface plasmon waves. This angle is dependent upon the sample in contact with the exposed surface of the metal layer.

In contrast to prior art SPR-based chemical sensors which utilize a single monochromatic incident light source and modulate the incident angle, the fiber optic SPR sensor of this invention employs a limited range of incident angles and uses incident light having multiple wavelengths. As used herein, the phrase "incident light having multiple wavelengths" means, at a minimum, two wavelengths, and is preferable a range of wavelengths sufficiently broad to encompass the resonance spectrum of the sample. For example, black body radiation or a white light source may serve as the incident light. Alternatively, two or more discrete wavelengths may be employed in the practice of the present invention. Furthermore, as used herein, the phrase "limited range of incident angles" means the range of propagating angles supported by a given optical fiber.

Suitable optical fibers of the present invention include commercially available fibers which support internal propagation of light by TIR. Such fibers may generally be characterized by three parameters: the optical fiber core material, the numerical aperture of the fiber, and the optical fiber core diameter. The choice of the optical fiber core material will effect the position of the resonance (i.e., where it occurs in the wavelength region). For example, a silica optical fiber with a refractive index of 1.46 permits measurements of effective refractive indices from about 1.32 to about 1.45, and may be experimentally observed as the resonance shifts from 400 nm up to 1000 nm. Other optical fiber core materials will similarly effect the position of the resonance. Thus, use of optical fiber core materials of a higher refractive index than silica will shift the dynamic range of the effective refractive indices to higher values. For example, sapphire, with a refractive index of 1.76, will result in a sensor with a dynamic range of effective refractive indices of from about 1.45 to about 1.75. Similarly, use of a plastic optical fiber core, such as a polymethylmethacrylite (PMMA) with a refractive index of 1.50, would permit measurements of effective refractive indices from about 1.33 to about 1.49. If an optical fiber core material with a lower refractive index than silica was employed, the dynamic range of the measurable sample refractive index would be shifted towards smaller values. The dynamic range of the fiber optic SPR sensors may also be modified by addition of appropriate dynamic range-controlling layers, as discussed in greater detail below.

The numerical aperture of the optical fiber determines the acceptance angle of light that is allowed to propagate in the fiber. In the practice of this invention, suitable numerical apertures may range from about 0.05 to about 0.6, and are preferably from about 0.2 to 0.4, and most preferably from about 0.25 to about 0.35. The numerical aperture also determines the internal propagation angles of the light propagating in the fiber. For example, a silica optical fiber with a numerical aperture of 0.3 supports internal propagating angles of light ranging from 90° to 78.5° (relative to the normal of the core/cladding interface), and thus the limited range of incident angles for this fiber would range from 90° to 78.5°. The core diameter of the fiber may vary depending upon the specific application. Preferably, the optical fiber core diameter ranges from about 1 micron to about 2000 microns, and more preferably from 100 microns to 600 microns, and most preferably from 200 microns to 400 microns.

As an optional component, one end of the optical fiber may have an element which reflects the light propagating within the fiber such that the light reverses its direction of propagation. A suitable element which may accomplish this function is a mirrored layer located on the end surface of the optical fiber core. For example, if light is directed into the optical fiber at a first end, and the mirrored layer is located at a second end of the fiber, light propagating toward the second end will be reflected (upon contact with the mirrored layer) back toward the first end of the optical fiber. Such mirrored layers may be adhered to the end surface of the optical fiber core by known techniques, such as by electron beam evaporation, thermal evaporation, sputtering, electrodeless plating, or adhering or gluing a suitable mirrored layer to the end of the fiber. Suitable materials for the mirrored layer including highly reflective metals, such as silver, gold and chrome. The mirrored layer should be of sufficient thickness to provide adequate reflectivity, and should not support SPR at the end of the fiber. A metal thickness of about 2000 Angstroms (or greater) generally provides sufficient reflectivity, and a metal thickness in excess of about 1000 Angstroms generally will not support SPR at the end of the fiber. The appropriate thickness for any given mirrored layer having the above characteristics may be readily determined by one skilled in this art.

Detection of a sample with the fiber optic SPR sensor of this invention is made, in part, by contacting the sample with the sensing area of the optical fiber. The sensing area is made by exposing a portion of the optical fiber core by removal of the surrounding cladding or cladding/buffer layers, and adhering an SPR supporting metal layer to the exposed optical fiber core. The SPR supporting metal layer of the optical fiber is then exposed to the sample of interest, and the refractive index of the sample is determined by the methods disclosed below.

The cladding or cladding/buffer layers of the optical fiber may be removed to expose a portion of the core by know techniques. For example, the cladding or cladding/buffer layers may be removed by a torch, or by chemical agents which etch away the cladding or cladding/buffer layers while preserving the fiber core material. Alternatively, the cladding or cladding/buffer layers may be removed by commercially available, mechanical strippers (e.g., Clausse, No-Nik Optical fiber Stripper, Edmond Scientific Catalog, Barrington, N.J.).

Once a portion of the optical fiber core is exposed, the SPR supporting metal layer is adhered to the exposed core. As used herein, the term "SPR supporting metal layer" means a highly reflective metal that supports SPR at the metal/sample interface, and has a permittivity constant wherein the real part of the permittivity is negative and its magnitude is greater than the magnitude of the imaginary part. Within the visible and near-IR region (400 nm–1000 nm), both silver and gold satisfy this criteria. However, if the above wavelength range is extended into the infrared, other metals, such as aluminum, copper and tantalum, may also be employed.

The SPR supporting metal layer is preferably adhered to the exposed portion of the optical fiber core to a thickness which will optimize the resonance curve - that is, to a thickness which makes the SPR resonance spectrum sharp. When the SPR supporting metal layer is silver, this layer is preferably adhered to the exposed core at a thickness of about 550 Angstroms. If a thinner thickness is used, the resonance spectra will substantially broaden, and if a thickness in excess of 600 Angstroms is employed, the resonance will severely diminish or disappear. One skilled in this art may readily determine the appropriate thickness of the SPR supporting metal layer for any given optical fiber/SPR supporting metal layer combination by varying the thickness to optimize the resonance curve.

A single optical fiber may contain one or more sensing areas, of the same or different geometry, and with the same or different SPR supporting metal layers. Such sensing areas may be located along the length of the optical fiber, at one end of the optical fiber, or both. In addition, while any portion of the optical fiber may serve as the sensing area, in a preferred embodiment the cladding or cladding/buffer layers are removed from the entire circumference of the optical fiber core, and the SPR supporting metal layer is symmetrically deposited on the exposed core to a uniform thickness.

An energy source which emits light having multiple wavelengths serves as the source of incident radiation. Generation of the incident radiation may be by any of a number of commercially available devices. For example, a tungsten halogen lamp provides radiation with a wavelength range that is sufficiently broad to encompass the resonance spectrum between 400 nm and 1000 nm. However, other white light sources can be employed. Moreover, best results may be obtained when the current and temperature of a white light source are controlled in order to minimize any background spectral variation. The energy source may be coupled into the optical fiber by use of commercially available optical fiber illumination instruments, such as an Oriel, Optical fiber Source for Radiometry (this specific instrument focuses white light emitted from a bulb into one end of the optical fiber).

Suitable detection devices of the present invention are capable of detecting the intensity of all or a portion of the wavelengths of light exiting the optical fiber. For example, when the fiber is connected to a optical fiber spectrograph, the light exiting the fiber is reflected off a grating towards a linear array detector. Upon reflectance off the grating, the light is linearly dispersed as a function of wavelength. Individual photodiodes in the array detector then measure the intensity along the length of the array detector, and detects the light intensity versus linear displacement (which is proportional to wavelength ). A spectrophotometer may also be employed to measure light intensity versus wavelength, or a circular variable interference filter wheel may be used in front of a photodetector. Such a filter wheel allows for a certain narrow bandpass of light which changes as a function of wheel rotation, and permits measurement of the spectral intensity of the light. Similar detection devices could employ a dispersing prism, linear variable interface filter, or individual interference filters when only a limited number of wavelengths are of interest.

By measuring the resonance spectrum, the complex refractive index of the sample in contact with the sensing area of the optical fiber sensor can be determined. A sample's complex refractive index includes both the real and imaginary refractive index components. The real component of a sample's complex refractive index is inversely proportional to the speed at which light propagates through the sample, and is generally considered the "true" refractive index of the sample. The imaginary component of a sample's complex refractive index is related to the sample's absorbance or attenuation of light. For example, by measuring the resonance spectrum of a solution containing sugar, the concentration of the sugar can be determined (assuming the sugar is the only varying analyte in the solution that caused the real refractive index of the sample to change). Such measurements have utility in the manufacture of sugar-containing beverages, as well as the alcohol content of a solution, or the hydrogenation of vegetable oil. Similarly, the fiber optic SPR sensor of this invention may be used to measure the absorbance of a sample. For example, use of a dye indicator for one or more specific analytes within a sample (such as acid/base dye indicators for pH and $CO_2$) may be employed.

In addition, the sensing area may optionally contain one or more additional layers adhered to the SPR supporting metal layer to yield effective refractive indices detectable by the sensor. Such additional layers may include a dynamic range-controlling layer and/or a reactive layer. A "dynamic range-controlling layer" is a layer adhered to the SPR supporting metal layer to alter the dynamic range of the fiber optic SPR sensor. For example, the dynamic range for a silica fiber, having a refractive index of 1.46, is about 1.32 to about 1.45. Adherence of a dynamic range-controlling layer of low refractive index (e.g., 1.2) to the SPR supporting metal layer will shift the dynamic range of the sensor to higher values (e.g., 1.42 to 1.55).

As used herein, the term "reactive layer" means a layer which interacts with the sample such that the effective refractive index detected by the sensor is altered. The addition of a reactive layer permits the manufacture of a fiber optic SPR sensor which is more sensitive to, or more selective for, a sample (or analyte within a sample). For example, suitable reactive layers include an antigen or antibody bound to the SPR supporting metal layer. This type of reactive layer will selectively bind the complementary antibody or antigen in the sample, increase the thickness of the reactive layer, and causes a shift in the effective refractive index measured by the sensor. In general, suitable reactive layers are altered in some manner upon contact with the sample, thus changing the effective refractive index measured by the sensor. Other reactive layers include sol-gel films and polymer coatings, and may be adhered to the SPR supporting metal layer by known techniques.

Figure 2:
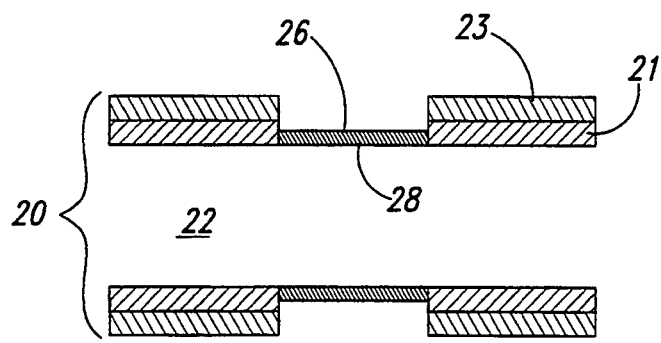
FIG. 2 illustrates an in-line transmission-based fiber optic SPR sensor of this invention.
Figure 3:
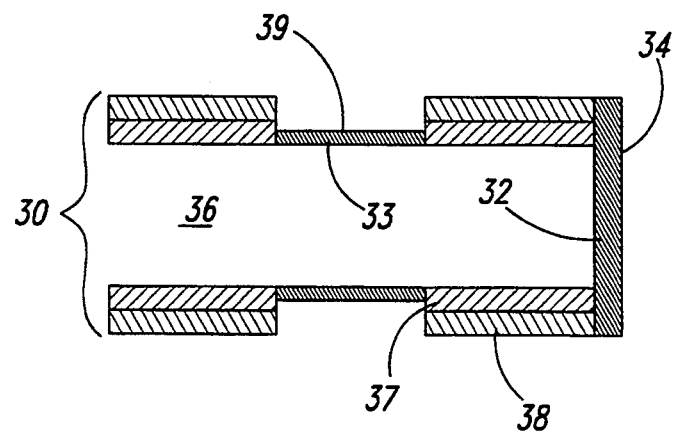
FIG. 3 illustrates a terminated reflection-based fiber optic SPR sensor.
Figure 4:
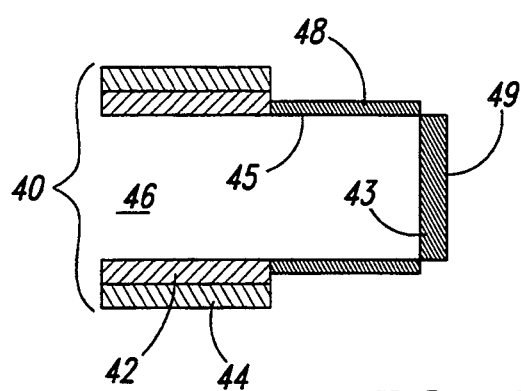
FIG. 4 illustrates a further embodiment of a terminated reflection-based fiber optic SPR sensor.

FIGS. 2–4 illustrate preferred embodiments of the fiber optic SPR sensor of this invention. In FIG. 2, an in-line transmission-based fiber optic SPR sensor is depicted. This sensor is made by removing a section of optical fiber cladding (21) and buffer (23) from core (22) of optical fiber (20), and depositing an SPR supporting metal layer (26) on exposed surface (28) of core (22).

In FIG. 3, a terminated reflection-based fiber optic SPR sensor is illustrated. In this embodiment, a mirrored layer (34) is adhered to the end of optical fiber (30). Specifically, the mirrored layer is in contact with end face (32) of optical fiber core (36), and covers cladding layer (37) and buffer layer (38) of the optical fiber. An SPR supporting metal layer (39) is adhered to an exposed surface (33) of core (36).

FIG. 4 illustrates a further embodiment of a terminated reflection-based fiber optic SPR sensor wherein the sensing area is located at the end of the optical fiber. Cladding layer (42) and buffer layer (44) are removed from optical fiber (40) to expose surface (45) of core (46). An SPR supporting metal layer (48) is adhered to exposed surface (45) of core (46). Mirrored layer (49) is in contact with end face (43) of core (46).

The following examples are offered by way of illustration, not limitation.

EXAMPLES

Example 1

Calculated SPR Shift Between Water and Sucrose Solution

Figure 5:
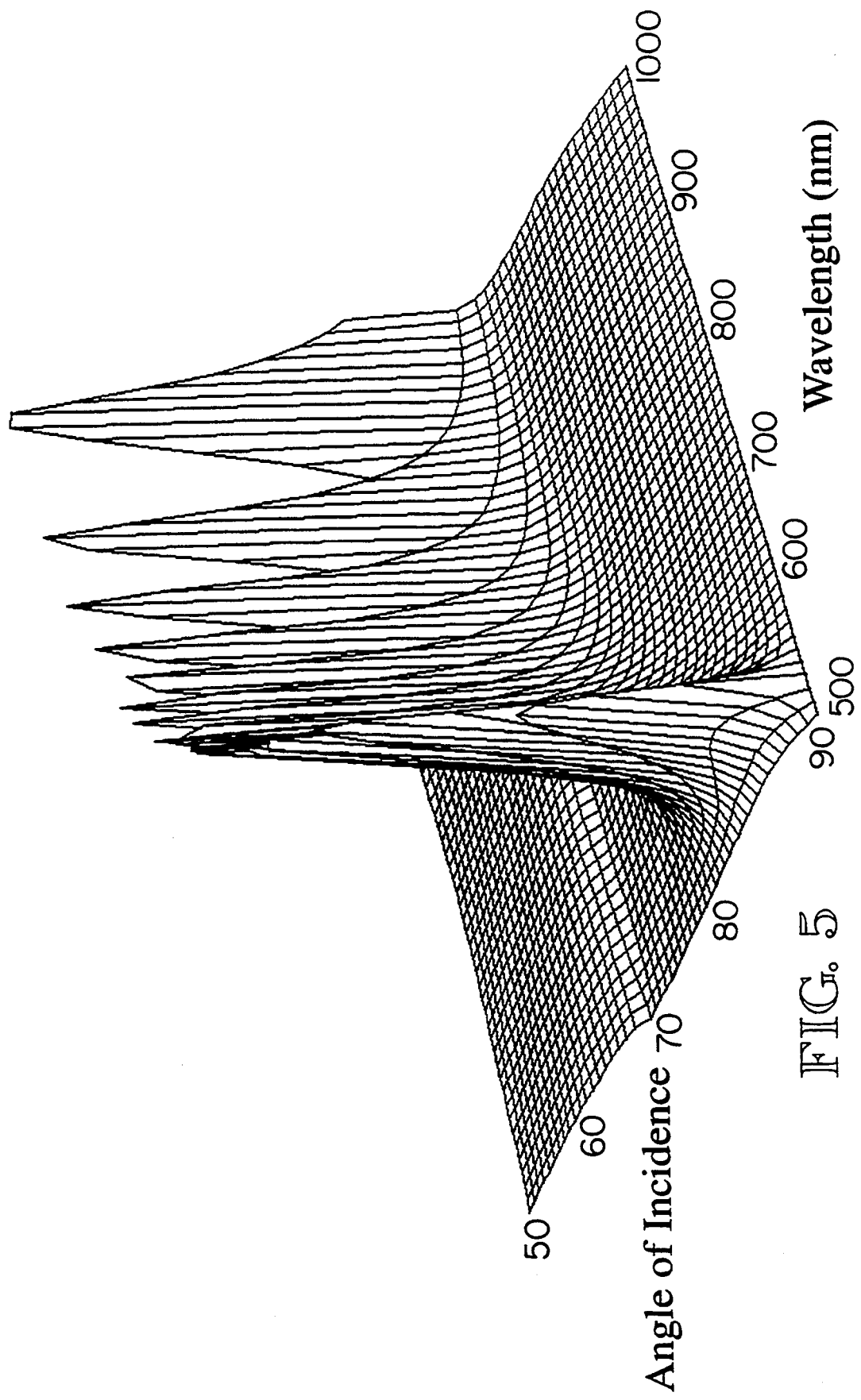
FIG. 5 is a calculated three-dimensional SPR reflection spectra for a bulk dielectric of water.
Figure 6:
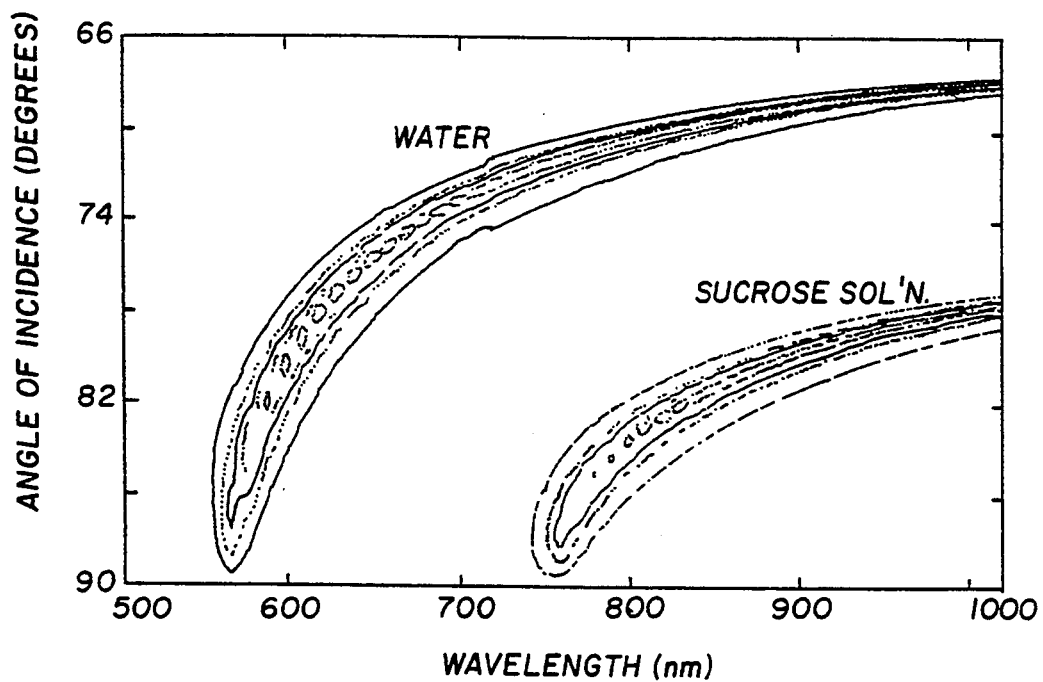
FIG. 6 is a contour plot of two theoretical three-dimensional SPR reflection spectra for water and a 37.1% sucrose solution.

A calculated three-dimensional SPR reflection spectra for a range of wavelengths (400–1000 nm) is illustrated in FIG. 5. This spectra was calculated using a matrix method to determine the fresnel reflection coefficients of a multilayered structure and assumes a silica optical fiber, a 550 Angstrom silver layer, a bulk sample of water, and TM polarized light. The refractive index values for silver silica and water was obtained from the literature (e.g., see Hass and Hadley, Optical Properties of Metals, *American Institute of Physics Handbook*, D. Gray ed., McGraw-Hill, New York, pp. 149–151, 1972; Querry et al., Water ($H_2O$), Handbook of Optical Constants of Solids II, E. Palik ed., American Press, Boston, pp. 1059–1077, 1991; Malitson, J.O.S.A. 55:1205–1216, 1965). The change in the SPR coupling angle as a function of wavelength (as illustrated in FIG. 5) is primarily due to the increased magnitude of the silver complex refractive index over the wavelength range of 400–1000 nm. This large change in silver refractive index (about one order of magnitude) is compared to the relatively small change in both the silica and water refractive indices (i.e., 0.019 and 0.128 index of refraction units, respectively). FIG. 6 depicts a contour plot of two calculated three-dimensional SPR reflection spectra for water and a sucrose solution (37.1% by weight) as the bulk sample media. This figure illustrates the resonance coupling angle dependency upon wavelength, and the three-dimensional SPR spectra dependence upon the bulk dielectric refractive index between the water and sucrose spectra.

Figure 7:
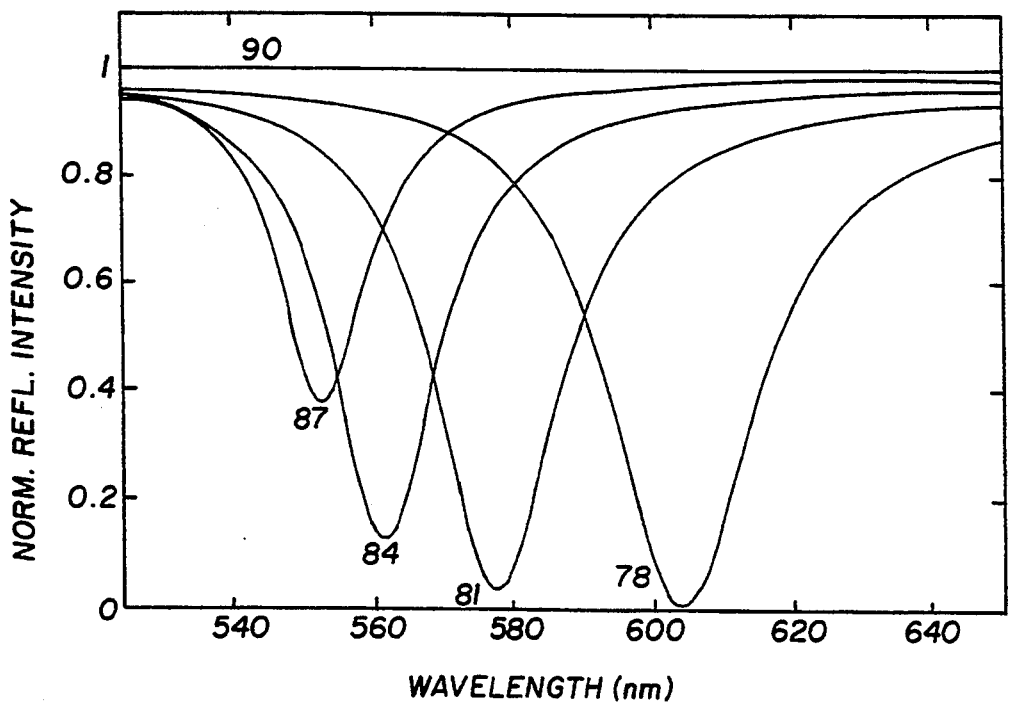
FIG. 7 is the calculated SPR spectra of reflected light intensity versus wavelength for a number of angles propagating inside a optical fiber sensor.

In order to model the spectrum of the SPR fiber optic sensors several factors must be considered, including: (1) the three dimensional SPR reflection spectra, (2) the number of reflections each propagating mode of undergoes, and (3) the density of propagating modes in the optical tibet sensor. FIG. 7 illustrates the theoretical SPR spectra (assuming a core diameter of 400 microns, a sensing area of 10 mm in length, and a constant light intensity over all wavelengths) of reflected intensity for one reflection versus wavelength for a number discrete angles propagating inside the fiber optical sensor (i.e., 90°, 87°, 84°, 81° and 78°). The number of reflections in the fiber sensor area, N, is a function of the mode propagation angle, $\theta$, the diameter of the fiber core, d, and the length of the sensing area, L, and is governed by the following equation:

$$N = L/d\tan\theta$$

Figure 8:
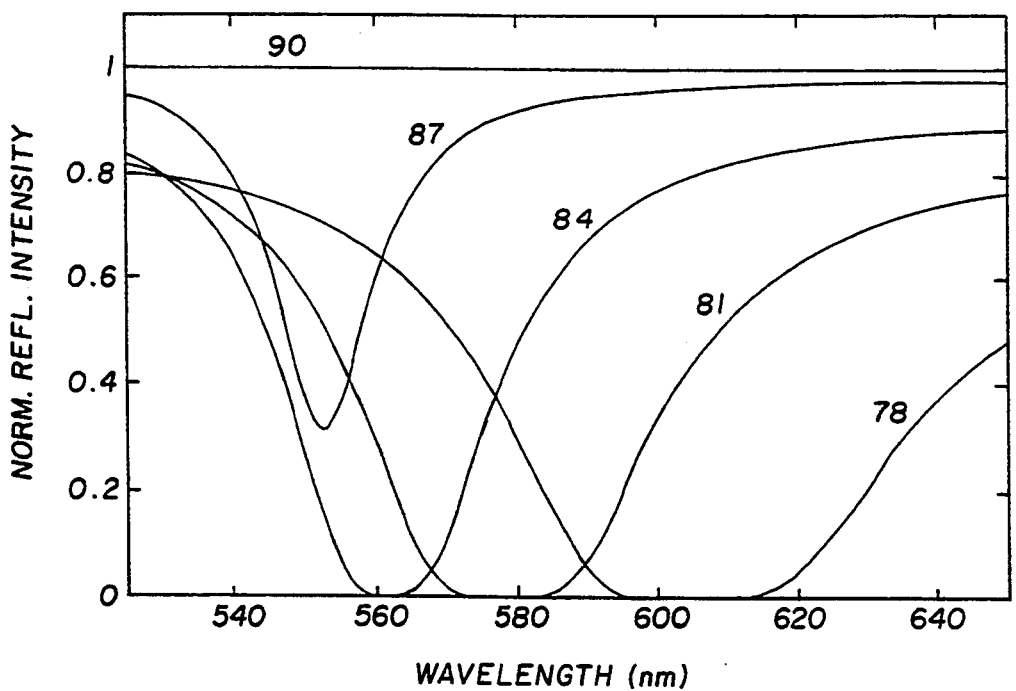
FIG. 8 is a calculated SPR spectra taking into account the number of reflections each angle encounters.

Thus, to determine the effective SPR spectra, taking into account the multiple reflections, the spectra for a single reflection is raised to the power of the number of reflections the specific propagating angle undergoes with the sensor interface. FIG. 8 illustrates the effective SPR spectra of intensity versus the wavelength for the propagating angles of FIG. 7. The spectra for the lowest order mode, 90°, travels parallel to the meridonial axis of the fiber and does not reflect off the interface. Therefore, the spectrum is that of the 90° spectrum of FIG. 6 raised to the power of zero, which yields a constant spectrum corresponding to no surface plasmon waves excited by the 90° propagating angle. Similarly, the smallest propagating angle in the fiber (i.e., 78°) has an effective spectra which is greatly broadened since it undergoes 5.31 reflections within the length of the sensing area.

Figure 9:
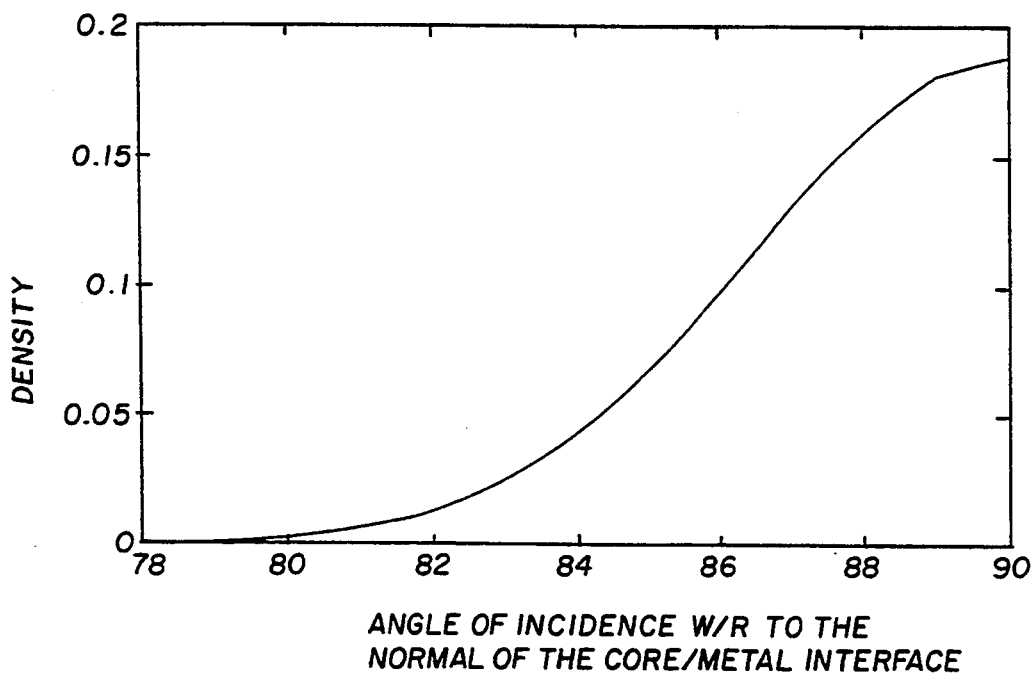
FIG. 9 is the non-linear distribution function of propagating angles within the optical fiber, and assumed to be Gaussian.
Figure 10:
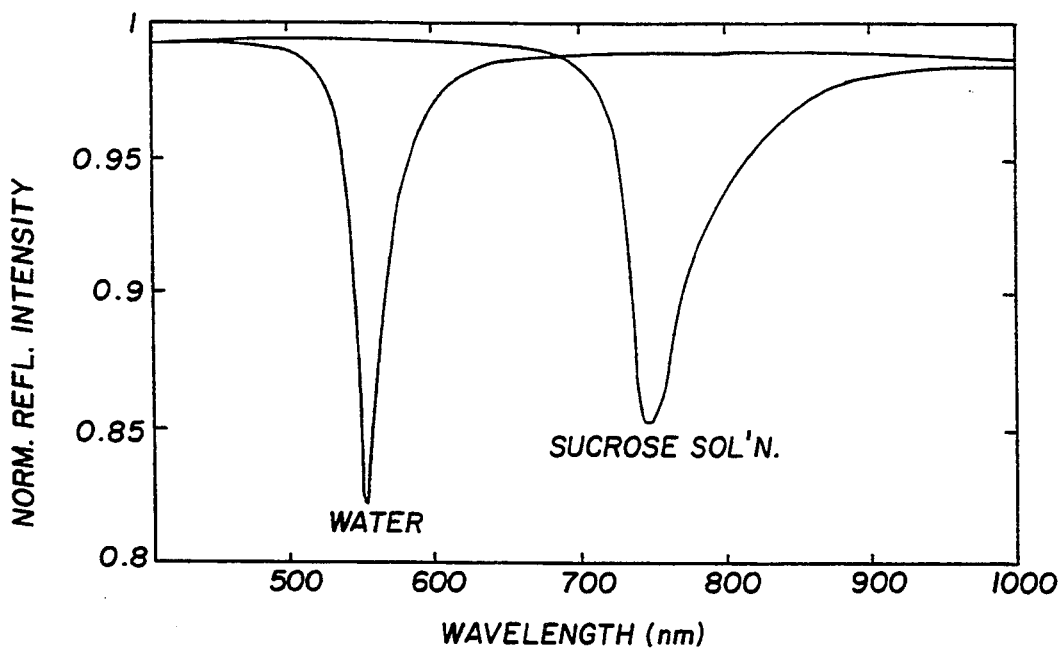
FIG. 10 is the calculated SPR spectra for a bulk refractive index of water and a 37.1% sucrose solution.

The SPR fiber optic signal detected at the output end of the fiber represents an accumulated spectra for the entire range of propagating angles, and not the spectra for any specific mode. Moreover, this signal is not an equally weighted average of all the angles propagating in the fiber. Thus, the theoretical signal must be weighted with the energy distribution function of all propagating angles in the fiber. For this purpose, the propagation angle density distribution function may be assumed to be Gaussian, spanning the range of the allowed propagating angles in the fiber is illustrated in FIG. 9. FIG. 10 represents the theoretical SPR fiber optic signal obtained by weight averaging the angular spectra of FIG. 8 with the density distribution of function of FIG. 9 for a bulk water sample and a 37.1% sucrose solution. Thus, an approximate 200 nm shift in SPR coupling wavelength is predicted, and corresponds to a change of 0.06 index of refraction units between the water and sucrose samples.

Example 2

In-Line Transmission-Based Fiber optic SPR Sensor

A silica/polymer fiber Type FP-400 UHT (3M, Minneapolis, Minn.), having a diameter of 400/600/760 microns (i.e., core, cladding and buffer diameters, respectively) and a numerical aperture of 0.3 was used in this example. The buffer and cladding layers were removed by a torch (Weber and Schultz, *Biosensors and Bioeletronics* 7:1930197, 1992), and the exposed core surface wiped with Dynasolve 100 (Dynaloy Inc., Hanover, N.J.). Specifically, three fiber optic sensors were fabricated by removing 6, 10 and 18 mm of the cladding/buffer layers along the length of three fibers. Each fiber was then mounted in an electron-beam evaporator such that the flux of the evaporated metal (silver) was perpendicular to the axis of the fiber. The fibers were rotated during silver deposition, resulting in a 550 Angstrom silver film deposited symmetrically about the fiber. The deposition process was monitored using a quartz crystal detector.

Figure 11:
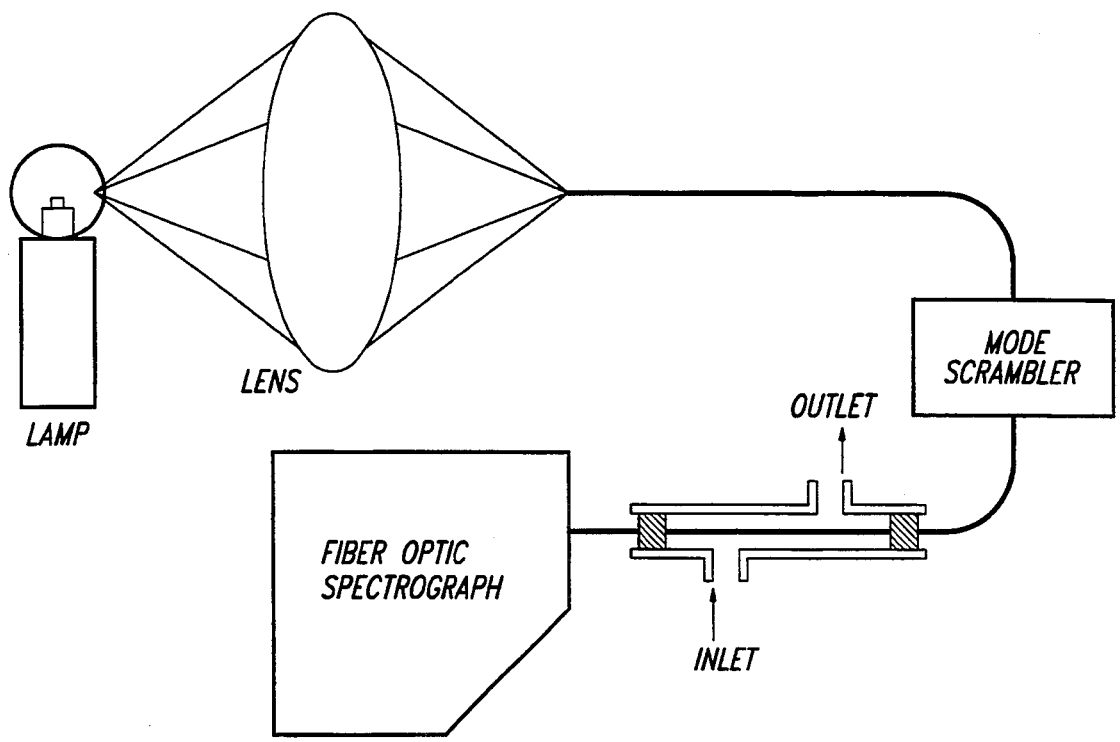
FIG. 11 illustrates a sensing apparatus of the present invention employing an in-line transmission-based fiber optic SPR sensor.

FIG. 11 illustrates the experimental set-up of this example. The three in-line transmission-based fiber optic SPR sensors were fabricated as disclosed above. The output of a tungsten halogen lamp was independently focused into each of the optical fibers. A mode scrambler was used to populate all modes of the optical fibers. The sensing area of the sensor was then enclosed by a three milliliter flow cell constructed using a syringe with two syringe stoppers and inlet and outlet ports. The output of the fiber optic SPR sensor was connected to a fiber optic spectrograph (American Holographic, Littleton, Mass.) via a SMA connector. The flat field grating is an American Holographic Model #446.33, which dispersed a range of wavelengths from 400 nm to 900 nm with a linear dispersion value of 20 nm/mm. The detector inside the spectrograph was a 1024-element CCD linear array detector. The theoretical wavelength resolution was determined by the linear dispersion value of the grating and the 25.4 micron width of the CCD element is 0.5 nm. A data acquisition board was used with an IBM compatible computer for automated acquisition.

Six sample solutions of high fructose corn syrup diluted with deionized water were prepared. The refractive indexes of these samples solutions were determined to be 1.333, 1,351, 1.364, 1.381, 1.393 and 1.404, respectively, using an Abbe Refractometer (Milton Roy Tabletop Refractometer 3L) at a 589 nm wavelength. The transmitted spectral intensity distribution was measured for each sensor while air was in the flow cell, and then measured again for each of the six prepared sucrose solutions by introducing 15 ml of each solution into the input port of the flow cell.

Figure 12A:
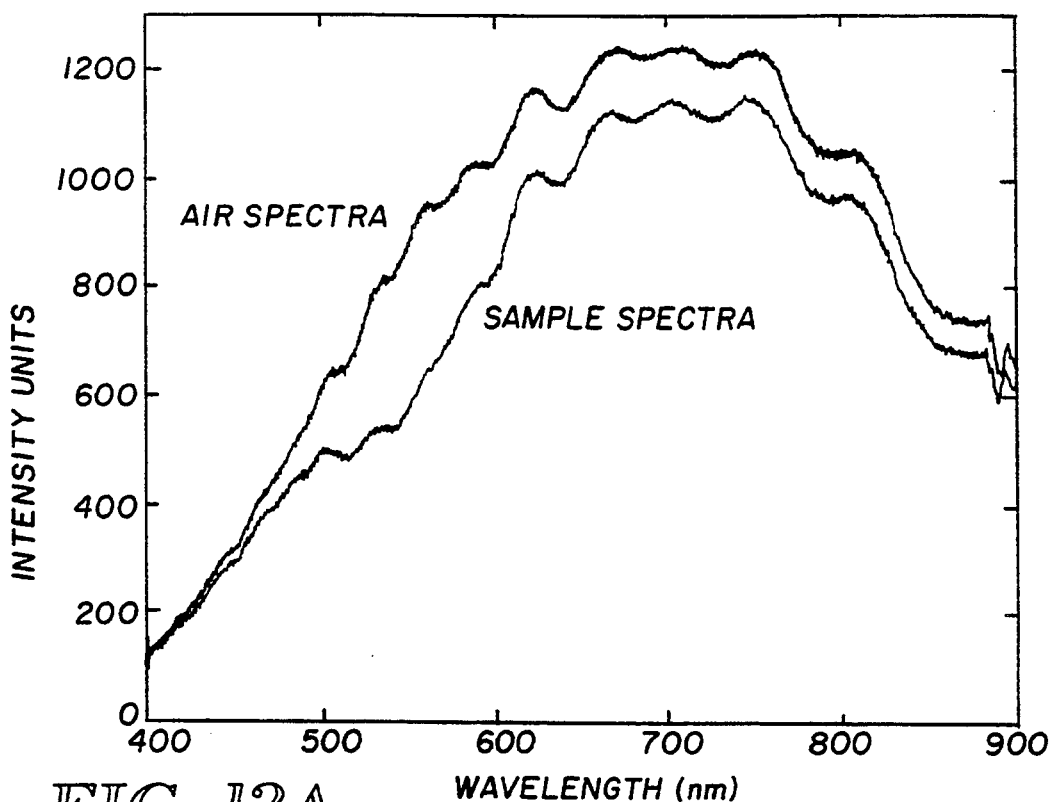
FIG. 12(a) illustrates representative air and sample SPR spectra.
Figure 12B:
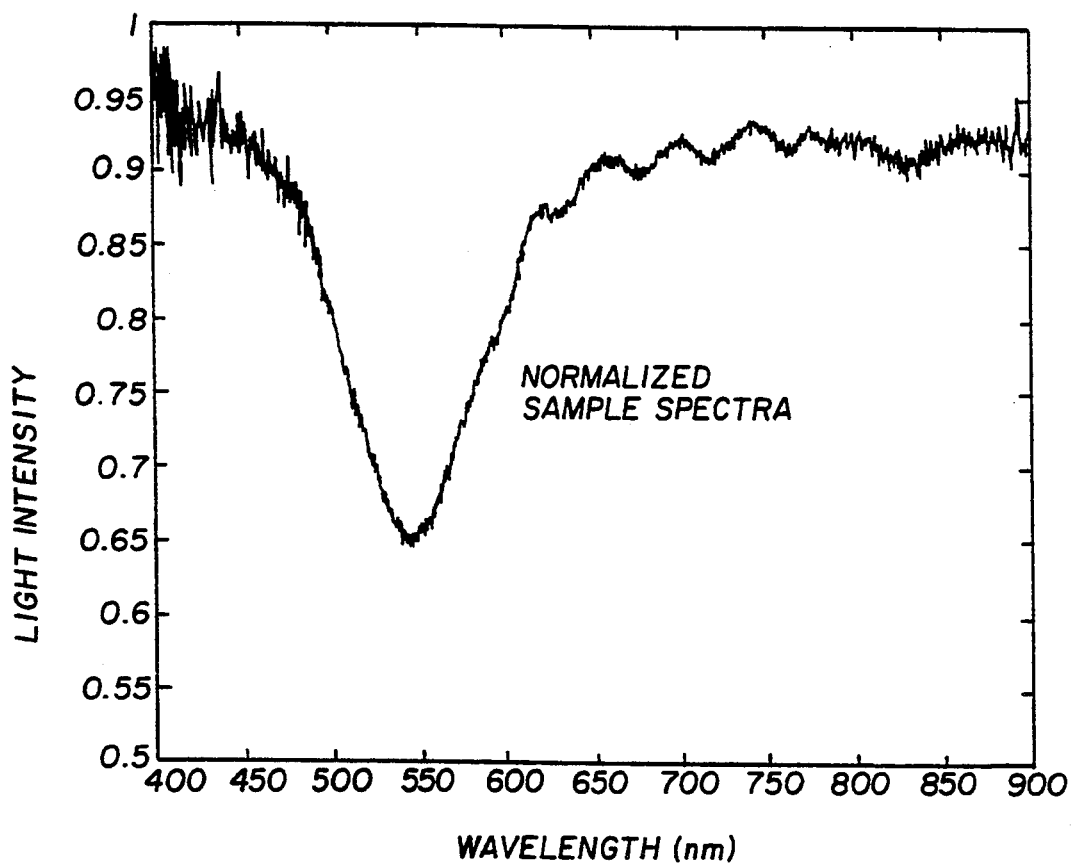
FIG. 12(b) depicts a normalized sample SPR spectra, and FIG. 12(c) are normalized SPR spectra collected using the in-line transmission-based fiber optic SPR sensor of Example 2.
Figure 12C:
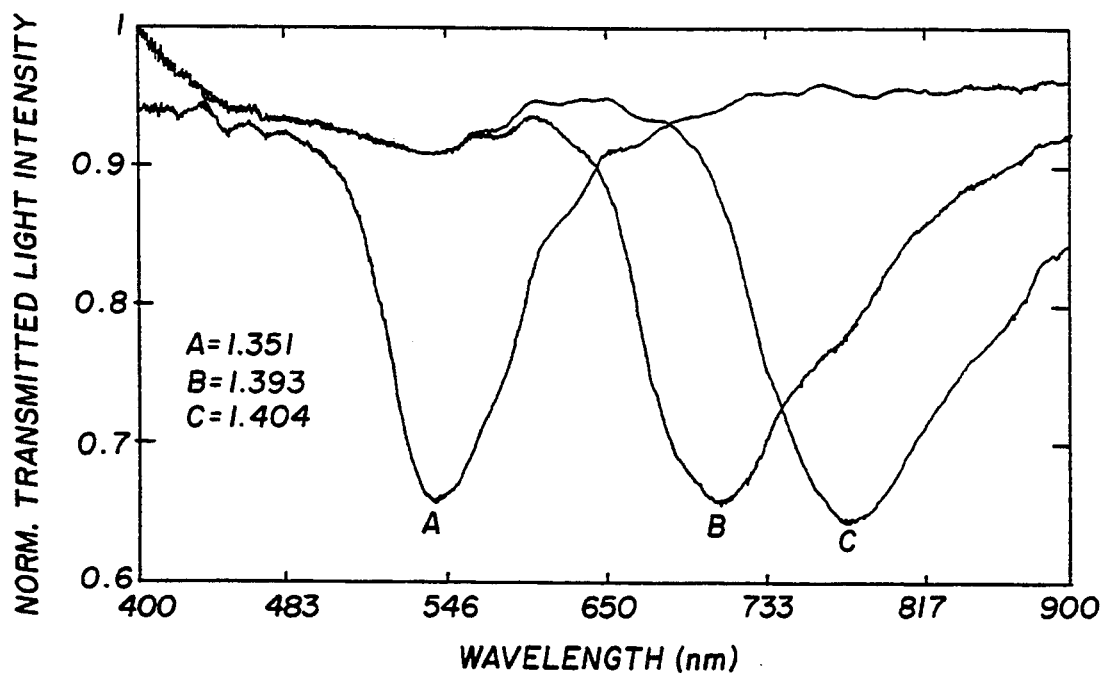

Since the intensity of the incident light was not constant for all wavelengths (400–900 nm), an air spectra was collected when the sensing area of the sensor was in contact with air (i.e., there is no surface plasmon resonance excitation in this wavelength range for air having a bulk refractive index of 1.00). The SPR spectra collected for each sample was normalized against the air spectra using the following equation:

$$N(\lambda) = 1 - [(I_{air}(\lambda) - I_{sample}(\lambda))/I_{air}(\lambda)]$$

where $I_{air}(\lambda)$ is the intensity of the air spectra at wavelength $\lambda$ and $I_{sample}(\lambda)$ is the intensity of the sample spectra at wavelength $\lambda$. A plot of $N(\lambda)$ versus $\lambda$ yields the normalized spectra. FIG. 12(a) illustrates a representative air and sample SPR spectra, and FIG. 12(b) depicts the normalized sample spectra according to the above equation. This calibration technique effectively normalizes the system transfer function, attributed by the light spectral output, the photo diode array spectral sensitivity, and the fiber spectral absorbance. FIG. 12(c) depicts the normalized transmitted light intensity as a function of wavelength measured by the 10 mm sensor for the fructose solutions with refractive indexes of 1.351, 1,393 and 1,404.

The resonance wavelength shift for the increasing bulk refractive indices of the sample is consistent with the calculated results illustrated in FIG. 10. However, it should be noted that the resonance spectra appears slightly broader than predicted. This observation is believed to be attributable, in least in part, to the large input fiber connected to the spectrograph (i.e., 400 microns), and thus the full spectrograph resolution is not optimized. It is believed that narrower resonance spectra may be achieved by reducing the diameter of the input optical fiber core to the spectrograph or by employing the use of a narrower slit.

Figure 13:
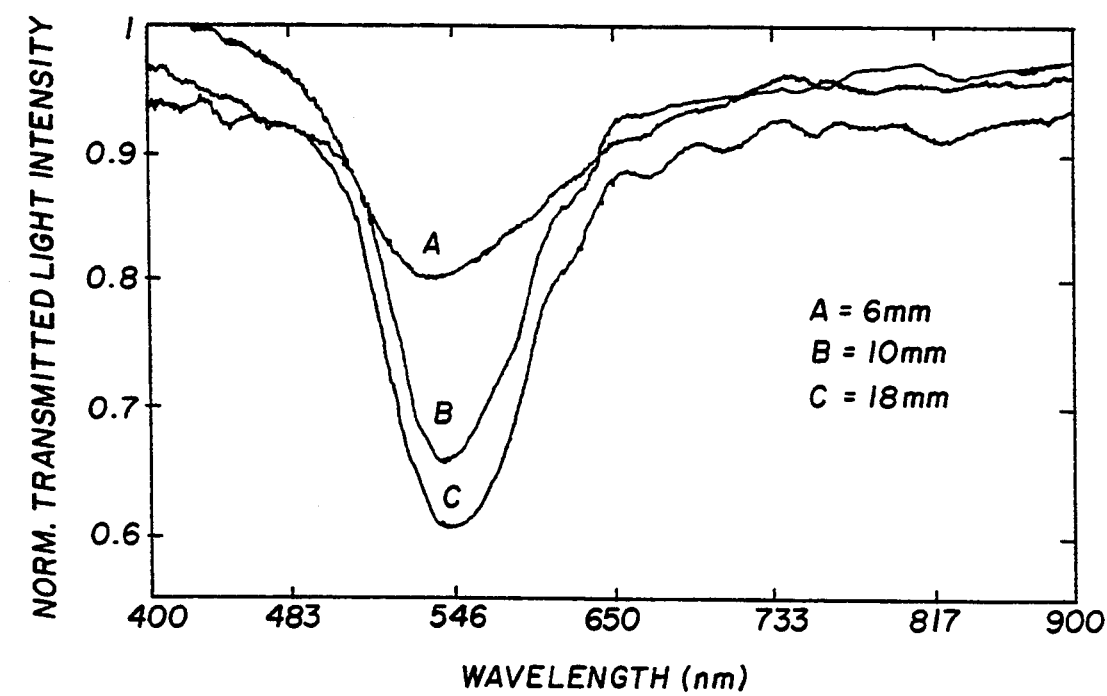
FIG. 13 is a plot of the normalized SPR optical fiber sensor spectra measured by the 6, 10, and 18 mm in-line fiber optic SPR sensors of Example 2.

FIG. 13 is a plot of the SPR optical fiber sensor spectra measured by the 6, 10 and 18 mm sensors for a single fructose solution (i.e., refractive index of 1.351). The transmitted spectral intensity distribution depends upon the length of the SPR sensing area as illustrated in FIG. 13, a longer sensing area resulted in a deeper observed resonance spectra. Thus, the size of the sensing area can be optimized, and primarily depends on the surface area of the sensing area, the diameter of the optical fiber core, and the numerical aperture. Due to the cylindrical geometry of the fiber, both TE and TM polarized light (with respect to the core/metal interface) are allowed to propagate in this multi-mode fiber. Thus, the expected optimal transmitted light intensity at resonance is 0.5 rather than 0.0, since SPR can only be excited with TM polarized light.

Figure 14:
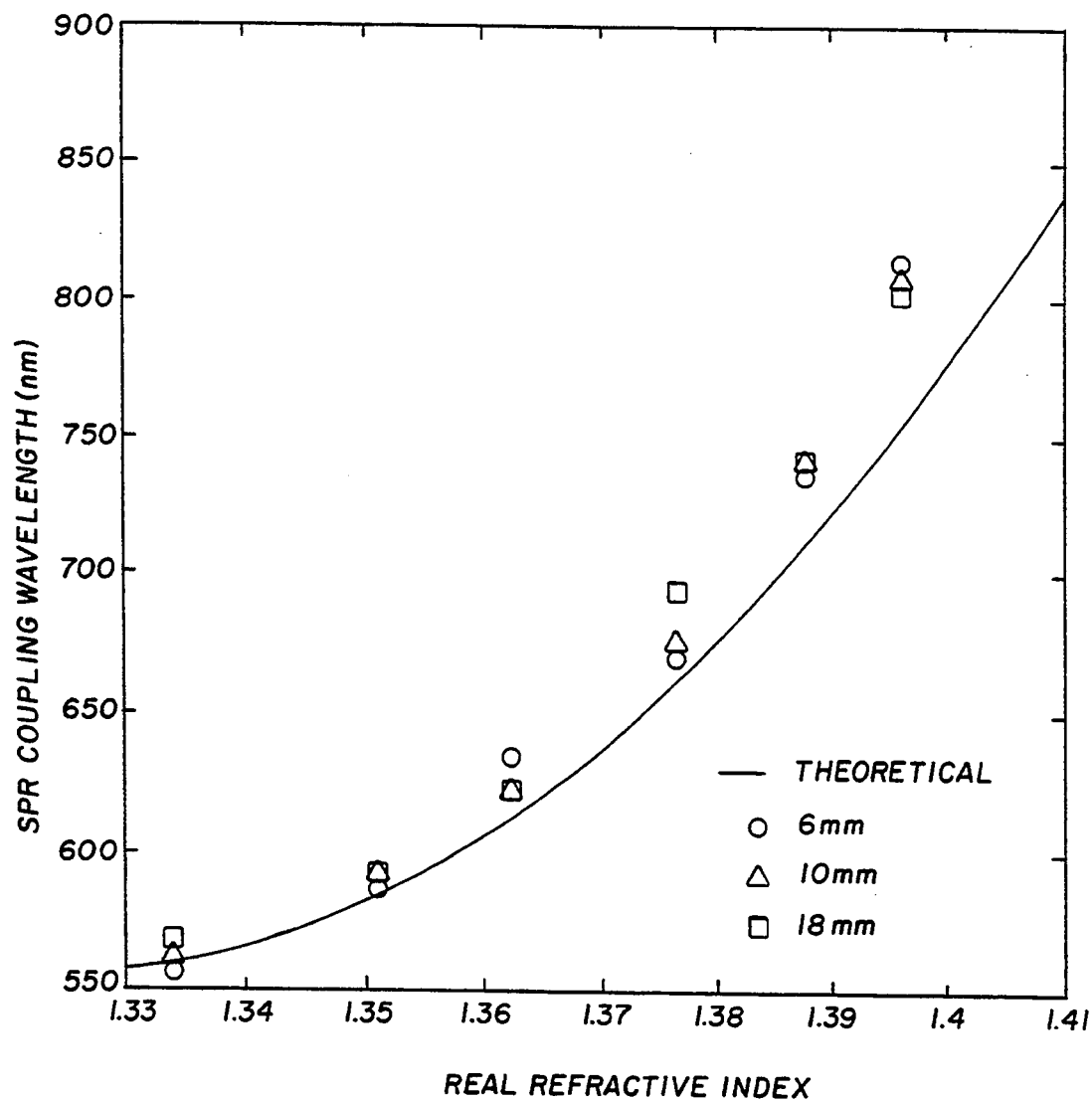
FIG. 14 depicts the calculated and experimentally determined SPR coupling wavelength versus the refractive index for the sucrose solutions of Example 2.

Theoretical and experimental SPR coupling wavelength versus the refractive index of the fructose solutions are plotted in FIG. 14 for the three SPR optical fiber sensors of FIG. 13. The response of all three sensors are in good agreement with the calculated shifts of Example 1. To plot the Abbe Refractometer measured refractive indices of the sample solutions in FIG. 14 the values were corrected for wavelength using the refractive dispersion measurement (Abbe Refractometer Operator's Manual and Dispersion Table, Milton Roy Company, Analytical Products Division, Rochester, N.Y., 1986). The theoretical sensitivity of the fiber optic SPR sensor to refractive index was calculated from the SPR wavelength response curve of FIG. 13. Because the response is non-linear, the sensitivity is a function of wavelength, with increased sensitivity at longer wavelengths. The theoretical sensitivity to refractive indices is $2.5 \times 10^{-4}$ at a wavelength of 500 nm, and $7.5 \times 10^{-5}$ at a wavelength of 900 nm, assuming an optimal wavelength resolution of the spectrograph of 0.5 nm, and the observed sensitivity at these wavelengths is in good agreement.

Example 3

Terminated Reflection-Based Fiber optic SPR Sensor

Figure 15A:
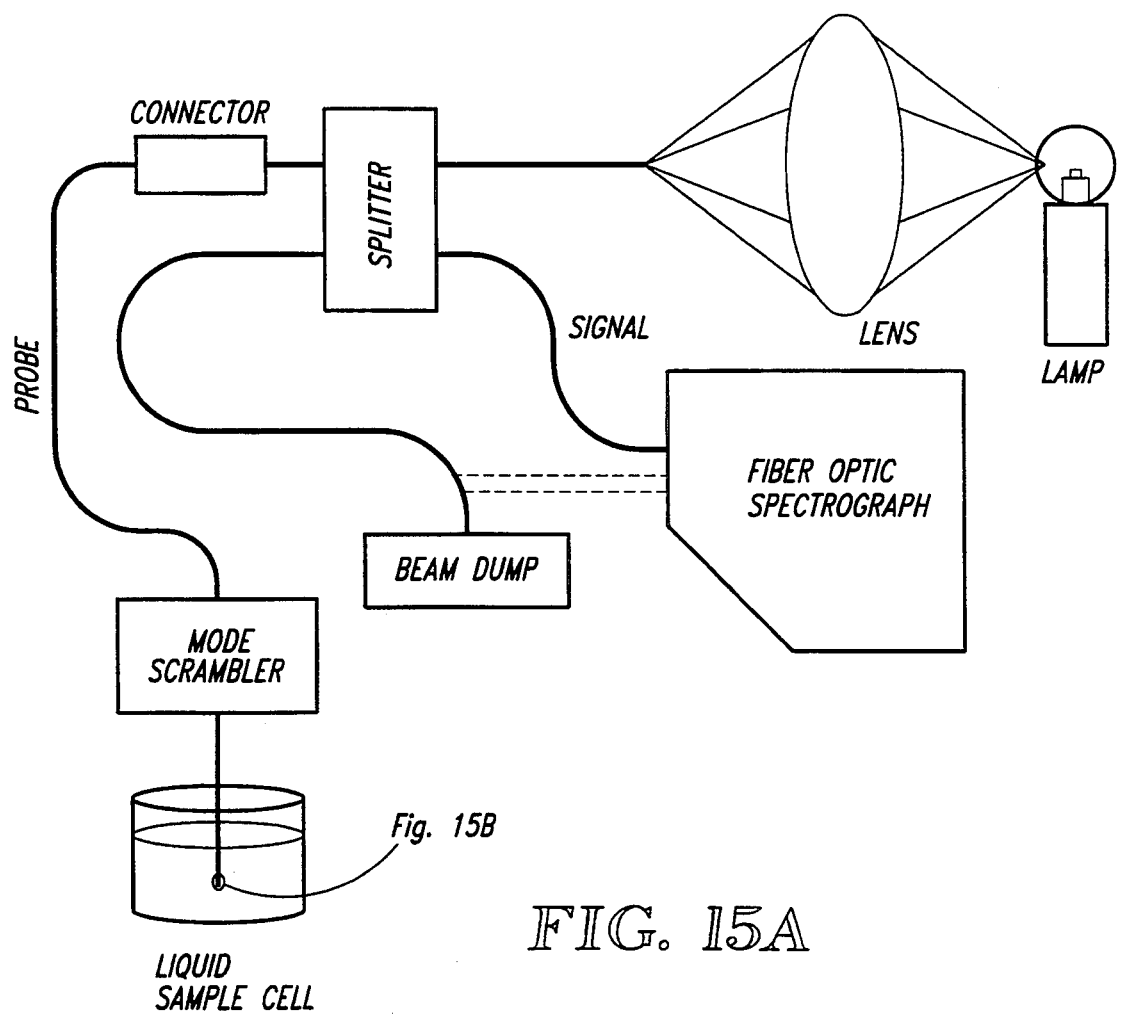
FIG. 15 illustrates a sensing apparatus of the present invention utilizing a terminated reflection-based fiber optic SPR sensor.
Figure 15B:
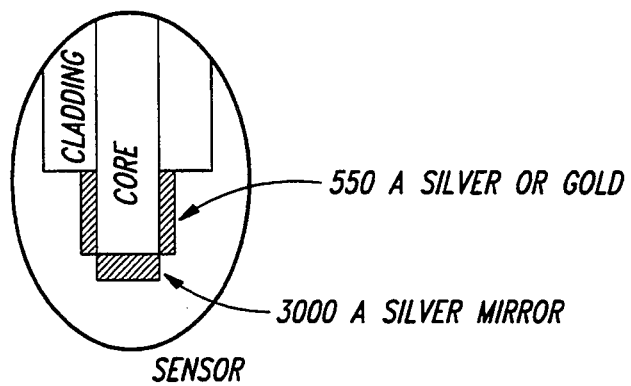

FIG. 15 illustrates a terminated reflection-based fiber optic SPR sensor of the present invention. This sensor is similar to the in-line transmission sensor described above, but uses a micro-fabricated mirror at the end of the optical fiber to internally reflect the light propagating through the fiber. In this embodiment, the light travels through the sensing area twice, thus the sensing length can be one half the length of the sensing area of the in-line transmission sensor.

The terminated reflection-based fiber optic SPR sensors were constructed by stripping off 1 cm of the cladding and buffer layers at the end of two separate silica optical fibers (0.3 numerical aperture, 400 micron core diameter). The fibers were then individually mounted vertically in an electron beam evaporator chamber such that the stripped end of each fiber was face down. An evaporated metal (silver) was then deposited on the stripped end face of each fiber, to a thickness of 3000 Angstroms by using a mask to prevent deposition on the exposed surface of the core. The fibers were then mounted in an electron beam chamber in the same fashion as the in-line fiber-optic sensors of Example 2, and either a silver or gold metal layer symmetrically deposited on the exposed core surface of the fibers to a thickness of 550 Angstroms.

In this example, light was coupled into a single branch of a 50:50 two way fiber optic splitter from a tungsten-halogen lamp. Fifty percent of the coupled light was then transferred to the sensor branch of the splitter. A SMA connector was used to connect the splitter to the SPR fiber optic sensor. The light was transmitted down the probe to the sensor area and reflected back up the optical fiber by the micro-fabricated mirror. The mirror thickness was such that SPR does not occur at the end of the optical fiber (in this example, the mirror thickness is 3000 angstroms). The returned light is then split again and connected to an optical fiber spectrograph to measure the spectral intensity of the signal light. The remaining arm of the splitter was index matched to a solution of glycerol so as to minimize back reflection. However, a reference signal could also be measured by using a spectrograph with two inputs, one for the signal and the other of a real time reference. The liquid samples of this experiment was six solutions containing glycerol at various concentrations to yield samples having different refractive indices.

Figure 16:
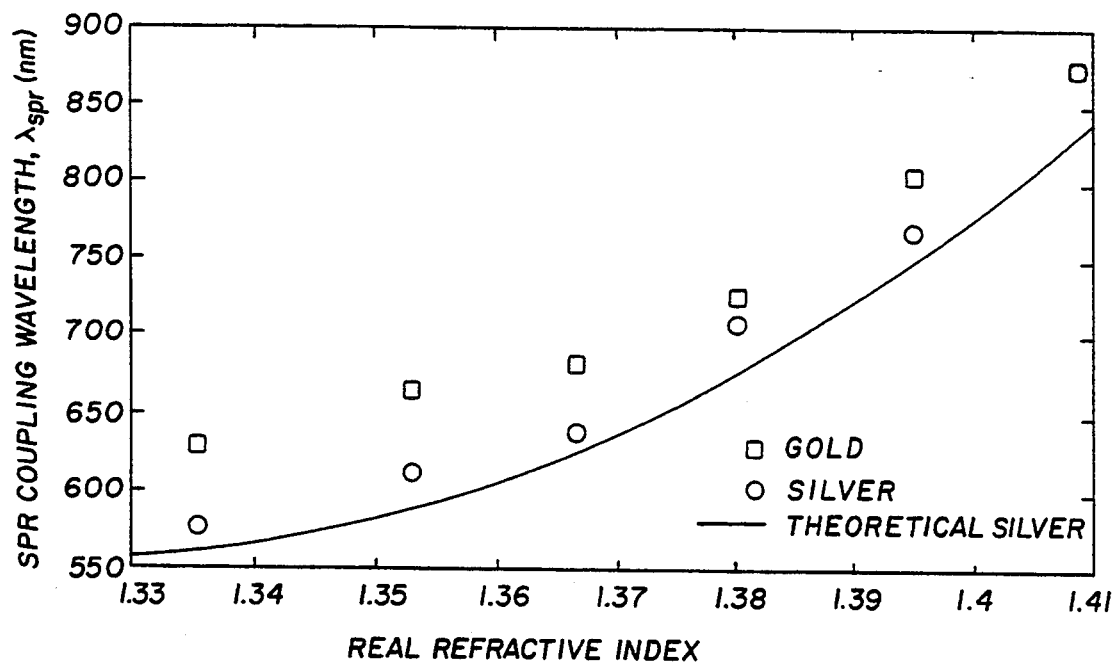
FIG. 16 illustrates the theoretical and experimentally observed SPR coupling wavelength versus the refractive index of the solutions detected in Example 3 utilizing an SPR supporting metal layer of either silver or gold.

The results obtained from the two terminated probes are illustrated in FIG. 16, and are consistent with the data and calculated results of an in-line transmission SPR fiber optic sensors. The wavelength offset observed between the terminated gold and silver probes is believed to be due to the difference in the permittivity constants between the two metals (see FIG. 16) of the SPR supporting metal layer.

Example 4

Immunoassay Utilizing Terminated Reflection-Based Fiber Optic SPR Sensor

This example illustrates the use of the fiber optic SPR sensor of Example 3 in combination with a reactive layer deposited on the surface of a SPR supporting gold layer. The observed shifts in the SPR spectra of Example 3 above (i.e., FIG. 16) towards larger coupling wavelengths, $\lambda_{spr}$, is due to increasing refractive indices of the bulk chemical sample. A similar shift can be caused by the presence of a thin film reactive layer between the metal and the sample. The adsorption of such a thin film layer (provided the thin film layer has a different refractive index than the bulk sample) will cause a shift in $\lambda_{spr}$. This is because the surface plasmon waves "sense" an effective refractive index, $n_{eff}$, that is representative of the combination of the refractive indices of the surface plasmon support layer, the thin film, and the thickness of the thin film. Changes in the film parameters (such as film thickness and/or complex refractive index) will cause a shift in $\lambda_{spr}$. These changes can be solved for by analyzing the properties of the measured SPR spectrum.

To illustrate this aspect of the present invention, protein solutions were prepared containing the following components: recombinant human Factor XIII (rhFXIII) expressed and purified from yeast (Zymo-Genetics, Inc., Seattle, Wash.), bovine serum albumin (BSA, Fraction V, Sigma, St. Louis, Mo.), and a rabbit anti-rhFXIII biotinylated polyclonal IgG preparation (rb-antiFXIII, Protein-A purified, est. 98% IgG). Both the rhFXIII and BSA samples were at a concentration of 10 mg/ml in Buffer A solution (pH 7,2, 2% sucrose, 0.1 mM EDTA.Na$_2$, 10 mM glycine) while the rb-antiFXIII was at 0.5 mg/ml in phosphate buffered saline (pH 7.4). All chemicals were purchased from Sigma Chemical.

Figure 17:
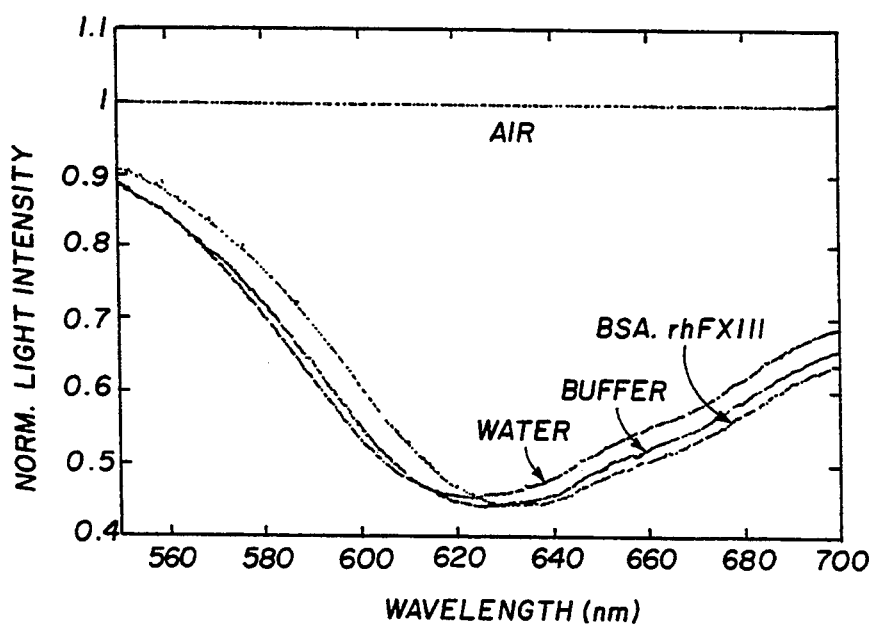
FIG. 17 illustrates the normalized SPR reflection spectra (referenced to air) for Buffer A, de-ionized water, BSA and rhFXIII.

FIG. 17 illustrates the SPR reflection spectra, referenced to air, for Buffer A, deionized water, BSA and rhFXIII which was obtained by dipping the terminated reflection-based fiber optic SPR sensor in the respective solution. The spectra was not effected by mechanical agitation or stirring of the test solution and the spectra for both the BSA and rhFXIII solutions shifted to the same extent. This indicates that the sensor is insensitive to the molecular weight of the protein (rhFXIII is 168 kD and BSA is 69 kD), but responsive to the mass of protein adsorbed to the surface of the sensing area.

Figure 18:
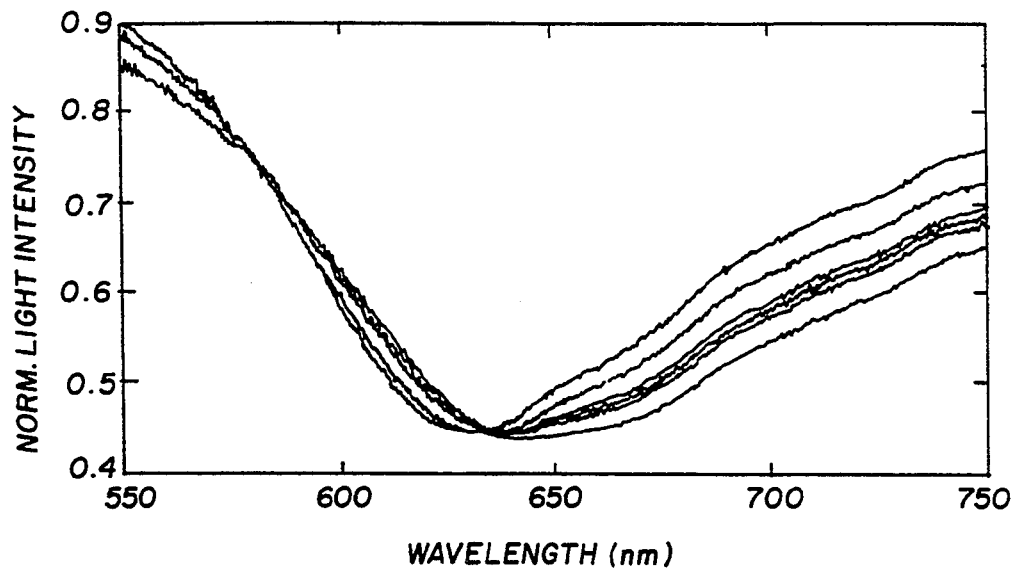
FIG. 18 illustrates the shift in the normalized SPR spectra due to binding of rb-antiFXIII over time (0–55 minutes).

The sensor was referenced to air, and tested in Buffer A and deionized water. The sensor was then coated with rhFXIII by placing the sensor in the rhFXIII solution until no spectral shift occurred. The sensor was then dipped into the BSA solution, and the interaction of the rb-antiFXIII was studied over a course of 55 minutes by placing the sensor in the antibody solution. The interaction of the polyclonal rb-antiFXIII with rhFXIII absorbed to the surface of the SPR supporting metal layer was found to be sufficient slow (hours) to permit measurement. The temporal shift in SPR spectra due to binding of rb-antiFXIII is illustrated in FIG. 18, and determination of the minima for each SPR spectra is depicted in FIG. 19.

Figure 19:
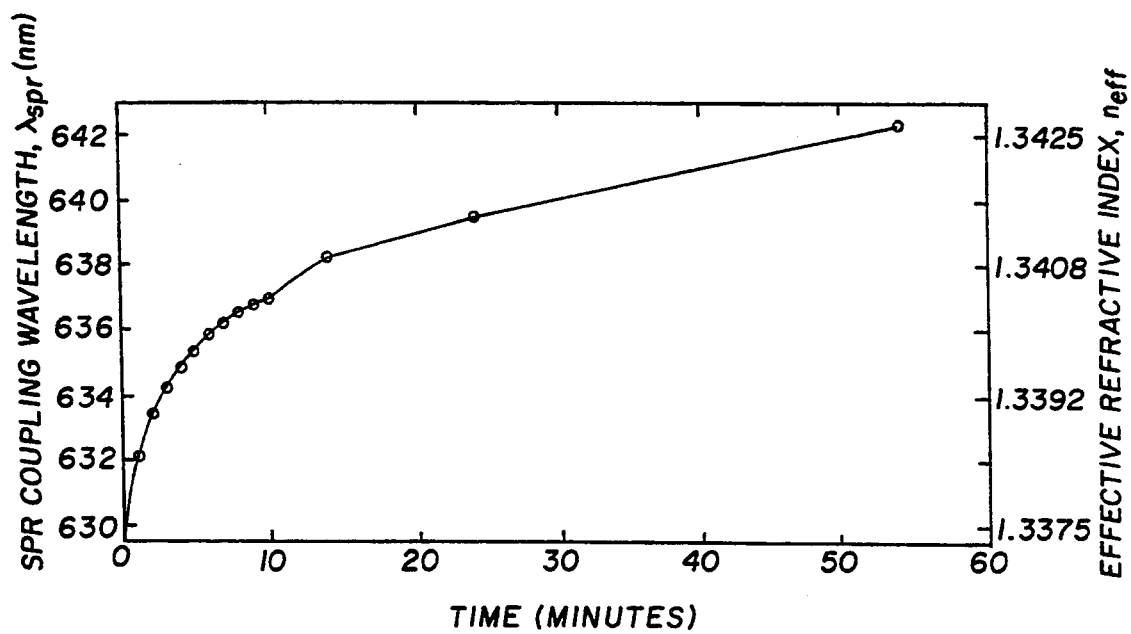
FIG. 19 illustrates the shift in the SPR spectra of FIG. 18 over time.

As illustrated by FIG. 19, over 50% of the observed response occurred within the first 10 minutes of exposure. The multi-phasic response behavior of the sensor is consistent with the nature of the polyclonal antibody use in this study, and represents the average response from a multitude of anti-ideotype IgGs with differing kinetic characteristics for rhFXIII. The sensor response was found to be reversible, as demonstrated by cleaning the probe with a 0.1N NaOH solution, and by subsequent spectral comparisons (for air and Buffer A) between the sensor prior to exposure to the test solutions versus subsequent to exposure.

From the foregoing, it will be appreciated that, although specific embodiments of the invention have been described herein for purposes of illustration, various modifications may be made without departing from the spirit and scope of the invention. Accordingly, the invention is not limited except as by the appended claims.

We claim:

1. A fiber optic surface plasmon resonance sensing apparatus, comprising:

a fiber optic surface plasmon resonance sensor, comprising an optical fiber having a core waveguide and a cladding or cladding/buffer layer surrounding the core waveguide, wherein the optical fiber has a first end and a second end and has at least one sensing area located between the first end and the second end or at the second end, wherein the sensing area is defined by a surface plasmon resonance supporting metal layer in contact with at least a portion of a surface of the optical fiber core waveguide free from the surrounding cladding or cladding/buffer layer;

a source of electromagnetic radiation of multiple wavelengths whose output is applied to the first end of the optical fiber core waveguide such that the radiation propagates from the first end towards the second end by total internal reflections and exists the optical fiber; and a detection device for monitoring the radiation exiting the optical fiber.

2. A fiber optic surface plasmon resonance sensing apparatus, comprising:

an in-line transmission-based fiber optic surface plasmon resonance sensor wherein the sensor comprises an optical fiber having a core waveguide and a cladding or cladding/buffer layer surrounding the core waveguide and having an input end and an output end, wherein the optical fiber has a sensing area located between the input end and output end, and wherein the sensing area is defined by a surface plasmon resonance supporting metal layer in contact with at least a portion of the optical fiber core waveguide free from the surrounding cladding or cladding/buffer layer;

a source of electromagnetic radiation of multiple wavelengths whose output is applied to the input end of the optical fiber waveguide such that the radiation propagates from the input end towards the output end by total internal reflections;

a detection device for monitoring the radiation exiting the output end of the optical fiber.

3. A optical fiber surface plasmon resonance sensing apparatus, comprising:

a terminated reflection-based optical fiber surface plasmon resonance sensor, wherein the sensor comprises an optical fiber having a core waveguide and a cladding or cladding/buffer layer surrounding the core waveguide and having an input/output end and a terminal reflection end, wherein the terminal reflection end is defined by an end face of the core waveguide in contact with a mirrored layer, wherein the optical fiber has a sensing area located between the input/output end and terminal reflection end, or at the terminal reflection end and wherein the sensing area is defined by a surface plasmon resonance supporting metal layer in contact with at least a portion of the optical fiber core waveguide free from the surrounding cladding or cladding/buffer layer;

a source of electromagnetic radiation of multiple wavelengths whose output is applied to the input/output end of the optical fiber waveguide, and wherein the radiation propagates from the input/output end towards the terminal reflection end by total internal reflections, internally reflects off the mirrored layer in contact with the end face of the core waveguide, and propagates back down the optical fiber waveguide by total internal reflections towards the input/output end;

a detection device for monitoring the radiation exiting the input/output end of the optical fiber waveguide.

4. The sensing apparatus of claim 3 wherein the sensing area of the sensor is located at the terminal reflection end of the optical fiber.

5. The sensing apparatus of any one of claims 1-4 wherein the sensing area further contains at least one additional layer adhered to the surface plasmon resonance supporting metal layer.

6. A method for detecting a sample, comprising:

contacting the sample with a optical fiber surface plasmon resonance sensor, wherein the sensor comprises an optical fiber core waveguide and a cladding or cladding/buffer layer surrounding the core waveguide, wherein the optical fiber has a first end and a second end and has at least one sensing area located between the first end and the second end or at the second end, wherein the sensing area is defined by a surface plasmon resonance supporting metal layer in contact with at least a portion of a surface of the optical fiber core waveguide free from the surrounding cladding or cladding/buffer layer, and wherein the sensing area of the sensor is in contact with the sample;

directing a source of electromagnetic radiation of multiple wavelengths into the first end of the optical fiber core waveguide such that the radiation propagates from the first end towards the second end by total internal reflections and exists the optical fiber, and wherein the propagating radiation interacts with the sensing area of the sensor which is in contact with the sample; and detecting the radiation exiting the optical fiber core waveguide.

7. A method for detecting a sample, comprising:

contacting the sample with an in-line transmission based optical fiber sensor, wherein the sensor comprising an optical fiber having a core waveguide and a cladding or cladding/buffer layer surrounding the core waveguide and having an input end and an output end, wherein the optical fiber has a sensing area located between the input end and output end, wherein the sensing area is defined by a surface plasmon resonance supporting metal layer in contact with at least a portion of the optical fiber core waveguide free from the surrounding cladding or cladding/buffer layer, and wherein the sensing area of the sensor is in contact with the sample;

directing a source of electromagnetic radiation of multiple wavelengths into the input end of the optical fiber waveguide such that the radiation propagates from the input end towards the output end of the optical fiber core waveguide by total internal reflections, and interacts with the sensing area of the sensor which is in contact with the sample; and detecting the radiation exiting the output end of the optical fiber waveguide.

8. A method for detecting a sample, comprising:

contacting the sample with a terminated reflection-based optical fiber surface plasmon resonance sensor, wherein the sensor comprising an optical fiber having a core waveguide and a cladding or cladding/buffer layer surrounding the core waveguide and having an input/output end and a terminal reflection end, wherein the terminal reflection end is defined by an end face of the core waveguide in contact with a mirrored layer, wherein the optical fiber has a sensing area located between the input/output end and terminal reflection end, or at the terminal reflection end wherein the sensing area is defined by a surface plasmon resonance supporting metal layer in contact with at least a portion of the optical fiber core waveguide free from the surrounding cladding or cladding/buffer layer, and wherein the sensing area is in contact with the sample;

directing a source of electromagnetic radiation of multiple wavelengths into the input/output end of the optical fiber core waveguide such that the radiation propagates from the input/output end towards the terminal reflection end by total internal reflections, internally reflects off the mirrored layer in contact with the end face of the core waveguide, and propagates back down the optical fiber core waveguide by total internal reflections towards the input/output end and wherein the propagating radiation interacts with the sensing area of the sensor which is in contact with the sample; and detecting the radiation exiting the input/output end of the optical fiber waveguide.

9. The method of claim 8 wherein the sensing area of the sensor is located at the terminal reflection end of the optical fiber.

10. The method of any one of claims 6-9 wherein the sensing area further contains at least one additional layer adhered to the surface plasmon resonance supporting metal layer.

11. An in-line transmission-based optical fiber surface plasmon resonance sensor, comprising an optical fiber having a core waveguide and a cladding or cladding-/buffer layer surrounding the core waveguide, and having an input end and an output end, wherein the optical fiber has a sensing area located between the input end and the output end, wherein the sensing area is defined by a surface plasmon resonance supporting metal layer in contact with at least a portion of the surface of the optical fiber core waveguide free from the surrounding cladding or cladding/buffer layer, and wherein the output end of the optical fiber does not have a mirrored layer in contact therewith which is capable of reflecting light propagating within the core waveguide such that the light reverse its direction of propagation and exits the input end.

12. A terminated reflection-based optical fiber surface plasmon resonance sensor, comprising an optical fiber having a core waveguide and a cladding or cladding-/buffer layer surrounding the core waveguide, and having and input/output end and a terminal reflection end, wherein the terminal reflection end is defined by an end face of the core waveguide in contact with a mirrored layer which is capable of reflecting light propagating within the core waveguide such that the light reverse its direction of propagation and exits the input-/output end and which does not support surface plasmon resonance, wherein the optical fiber has a sensing area located between the input/output end and terminal reflection end or at the terminal reflection end, and wherein the sensing area is defined by a surface plasmon resonance supporting metal in contact with at least a portion of the surface of the optical fiber core waveguide free from the surrounding cladding or cladding-/buffer layer.

13. The sensor of claim 12 wherein the sensing area of the sensor is located at the terminal reflection end of the optical fiber.

14. The sensor of any one of claims 11-13 wherein the sensing area further contains at least one additional layer adhered to the surface plasmon resonance supporting metal layer.

* * * * *

UNITED STATES PATENT AND TRADEMARK OFFICE
CERTIFICATE OF CORRECTION

PATENT NO. : 5,359,681
DATED : October 25, 1994
INVENTOR(S) : Ralph C. Jorgenson and Sinclair S. Yee It is certified that error appears in the above-indentified patent and that said Letters Patent is hereby corrected as shown below:

In column one, after the heading, "FIBER OPTIC SENSOR AND METHODS AND APPARATUS RELATING THERETO", and before the subtitle, "TECHNICAL FIELD", please insert the following sentence:

--This invention was made with government support under grant number EEC8415075 awarded by the National Science Foundation. The government has certain rights in the invention.--

Signed and Sealed this

Twenty-ninth Day of August, 1995

Attest:

BRUCE LEHMAN

*Attesting Officer*     *Commissioner of Patents and Trademarks*